US010983068B2

(12) United States Patent
Hunt et al.

(10) Patent No.: US 10,983,068 B2
(45) Date of Patent: Apr. 20, 2021

(54) SYSTEMS AND METHODS FOR MICROWAVE JAMMING OF MOLECULAR RECOGNITION

(71) Applicant: Georgia Tech Research Corporation, Atlanta, GA (US)

(72) Inventors: William Hunt, Decatur, GA (US); Kyle Spencer Davis, Cohutta, GA (US); Michelle LaPlaca, Atlanta, GA (US); Chris Ward, Atlanta, GA (US); John Alexander Herrmann, Suwanee, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 868 days.

(21) Appl. No.: 14/377,881

(22) PCT Filed: Feb. 14, 2013

(86) PCT No.: PCT/US2013/026193
§ 371 (c)(1),
(2) Date: Aug. 11, 2014

(87) PCT Pub. No.: WO2013/123232
PCT Pub. Date: Aug. 22, 2013

(65) Prior Publication Data
US 2015/0041457 A1    Feb. 12, 2015

Related U.S. Application Data

(60) Provisional application No. 61/598,675, filed on Feb. 14, 2012.

(51) Int. Cl.
| G01N 22/00 | (2006.01) |
| G01N 33/53 | (2006.01) |
| A61L 2/12 | (2006.01) |
| A61N 5/02 | (2006.01) |
| A61N 5/04 | (2006.01) |
| C12N 13/00 | (2006.01) |

(52) U.S. Cl.
CPC .............. G01N 22/00 (2013.01); A61L 2/12 (2013.01); A61N 5/022 (2013.01); A61N 5/045 (2013.01); C12N 13/00 (2013.01); G01N 33/53 (2013.01)

(58) Field of Classification Search
None
See application file for complete search history.

(56) References Cited

U.S. PATENT DOCUMENTS

| 5,463,226 A | 10/1995 | Matsuzaki |
| 6,421,550 B1 | 7/2002 | Bridges et al. |
| 2005/0139485 A1 | 6/2005 | Brooks et al. |
| 2007/0284241 A1 | 12/2007 | Osman |
| 2009/0001262 A1 | 1/2009 | Visser et al. |
| 2009/0131926 A1 | 5/2009 | Rusin et al. |
| 2010/0114086 A1 | 5/2010 | Deem et al. |

FOREIGN PATENT DOCUMENTS

WO    2002077607 A2    10/2002

OTHER PUBLICATIONS

Desyatnik et al. Phys . Chem. Chem. Phys., 2005, 7 , 1708-1715.*
Zelinski et al. Process Biochemistry, vol. 42, 8, 2007, 1250-1253.*
Bumel et al. Journal of Chemical Physics 84, 2604-2614, 1986.*
Gerry et al. Database CaPlus, AN 1989:642694, 1989.*
Coxetal. Database Caplus, AN 1981:199848, 1981.*
Hobzaetal. Database CaPlus, AN 1981:145469, 1981.*
Owen et al. Database CaPlus, AN 1976:576373, 1976.*
Mullin et al. Database Caplus, AN 2009:986111.*
M. Zielinski et al. Process Biochemistry 42 (2007) 1250-1253.*
International Preliminary Report in related PCT Application No. PCT/US2013/026193, dated Aug. 28, 2014.
International Search Report dated May 13, 2013.
Birge, RR, et al., "Role of Calcium in the Proton Pump of Bacteriorhodopsin: Microwave Evidence for a Cation-Gated Mechanism," The Journal of Physical Chemistry, 1996, vol. 100, No. 23, pp. 9990-10004.
Oliver, CM, et al., "Microwave Synthesis and Evaluation of Phenacylhomoserine Lactones as Anticancer Compounds That Minimally Activate Quorum Sensing Pathways in Pseudomonas Aeruginosa," J. Med. Chem 2009, vol. 52, pp. 1569-1575.
Weintraub, ST, et al., "Evaluation of the Necessity for Rapid Inactivation of Brain Enzymes Prior to Analysis of Norepinephrine, Dopamine and Serotonin in the Mouse," Lice Sciences. Oct. 2, 1975, vol. 17, pp. 1423-1428.
Song, X, et al., "Microwave Induces Apoptosis in A549 Human Lung Carcinoma Cell Line," Chinese Medical Journal, 2011, vol. 124, No. 8, pp. 1193-1198.

* cited by examiner

*Primary Examiner* — Michael L Borin
(74) *Attorney, Agent, or Firm* — Troutman Pepper Hamilton Sanders LLP; Ryan A. Schneider; Dustin B. Weeks

(57) ABSTRACT

Systems and methods include directing limited frequencies of microwave signals toward target molecules, driving a motion of the target molecules to impact molecular recognition. In one implementation, a microwave spectra associated with the rotational modes of a target molecule is obtained. From peaks in the spectra, a mode of molecular movement is identified and a microwave signal profile is generated for driving a motion of binding portions of the molecule associated with the identified mode. Microwave signals are generated based on the signal profile for output by antennas. For example, the microwave signals can be can be used to impede the binding of quorum sensing molecules by receptors of *P. aeruginosa*. In one implementation, the antennas can be placed in a catheter for placement in a patient. In another implementation, the antennas can be placed in a sleeve or other device for use adjacent to the skin of a patient.

20 Claims, 14 Drawing Sheets

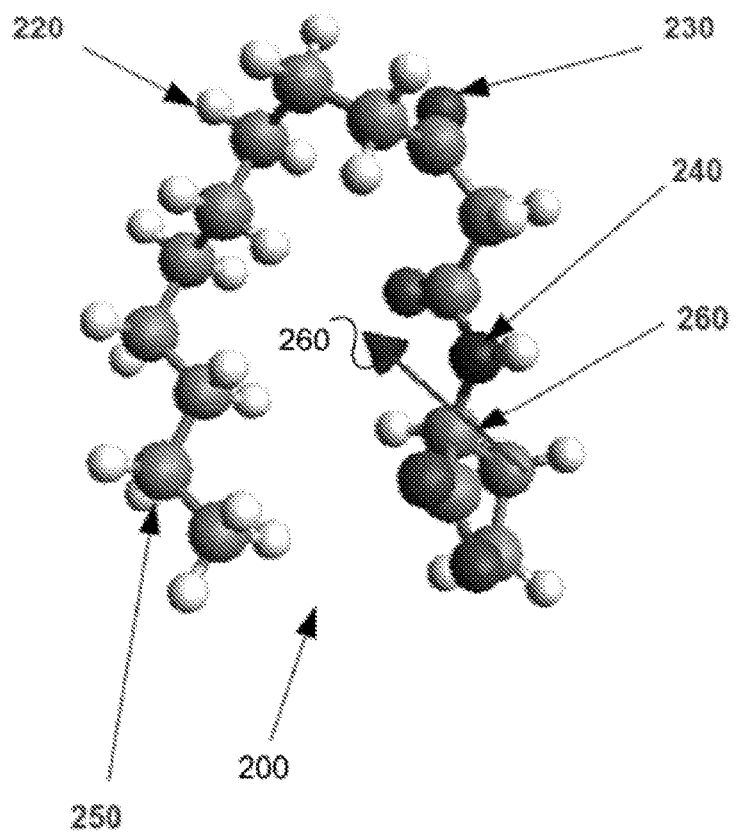
N-dodecanoyl-L-Homoserine lactone ("C12")
Quorum Sensing Molecule
Fig. 2A
Fig. 2B
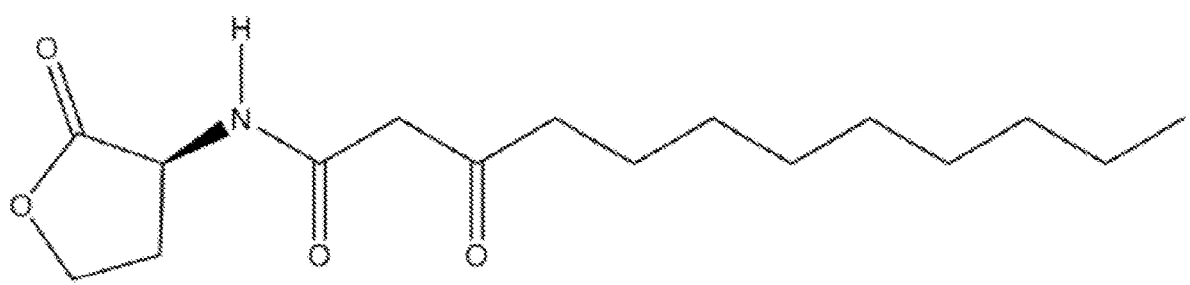

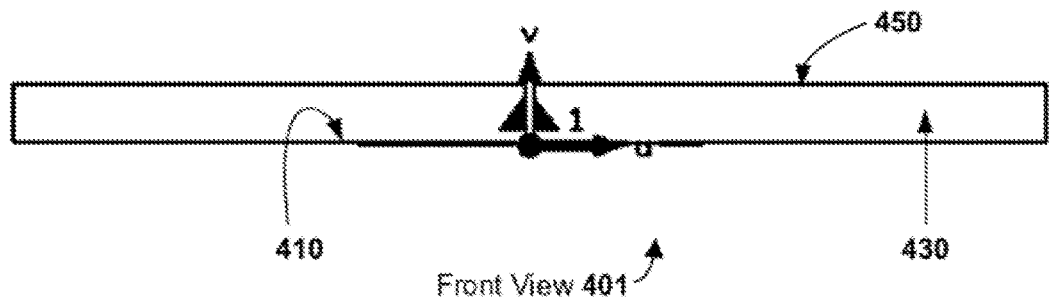
Front View 401
Fig. 7A
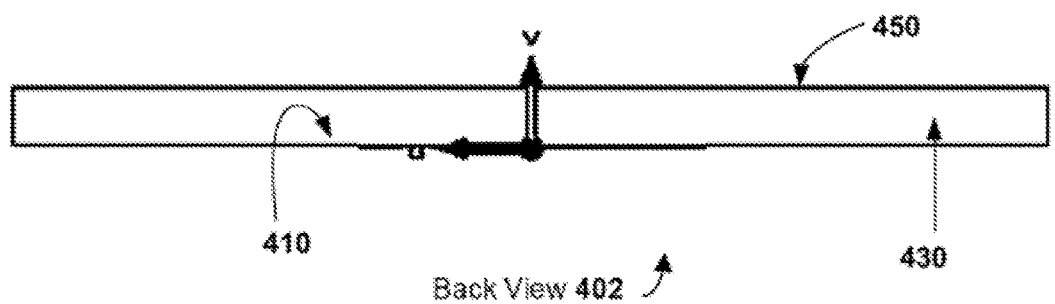
Back View 402
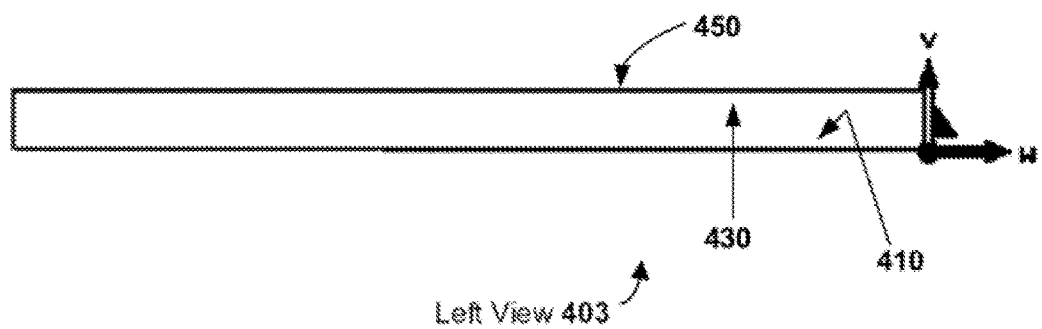
Left View 403
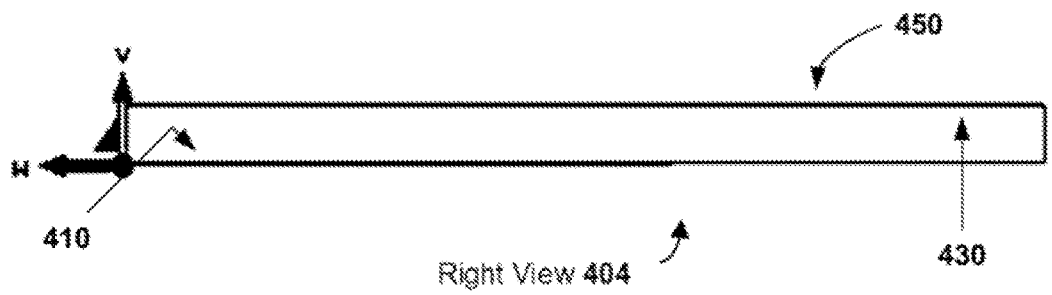
Right View 404

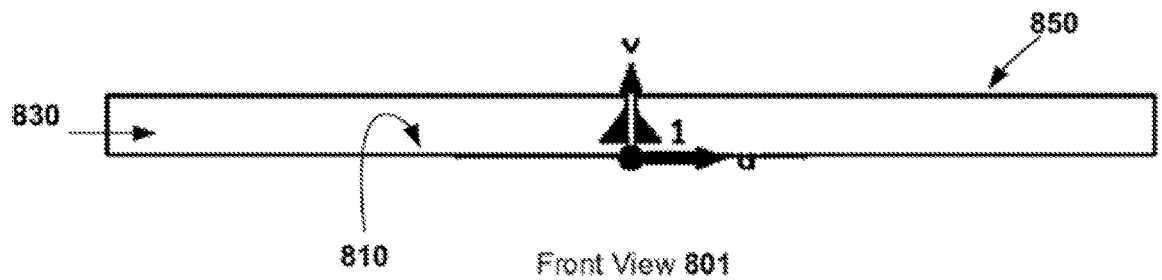
Front View 801
Fig. 8A
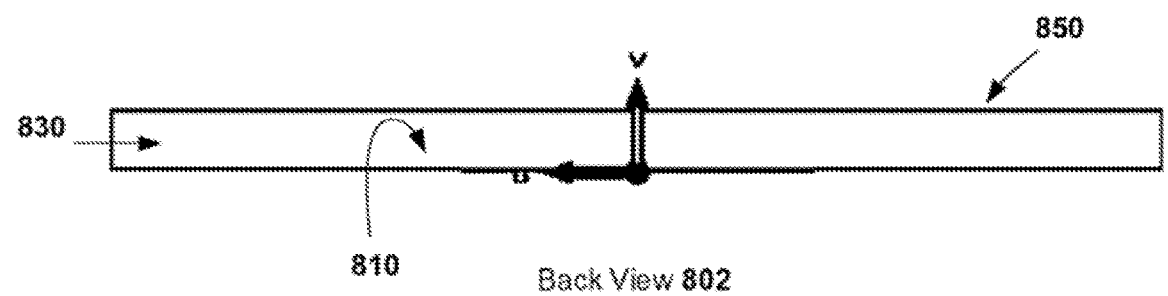
Back View 802
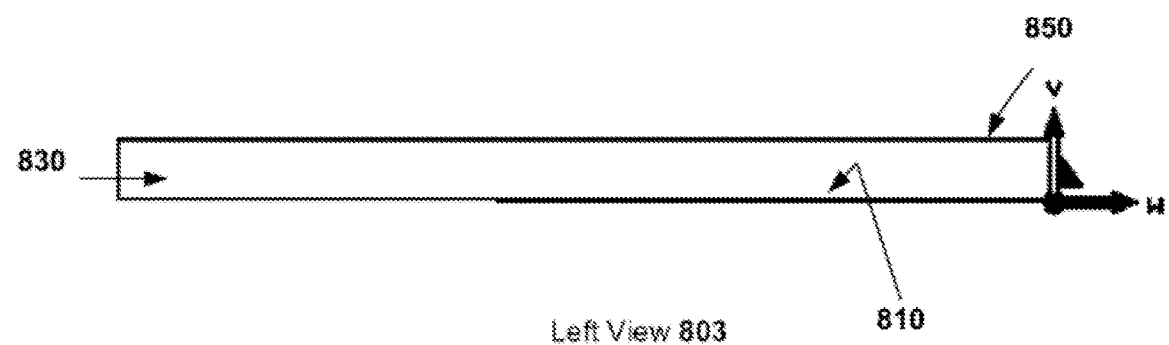
Left View 803
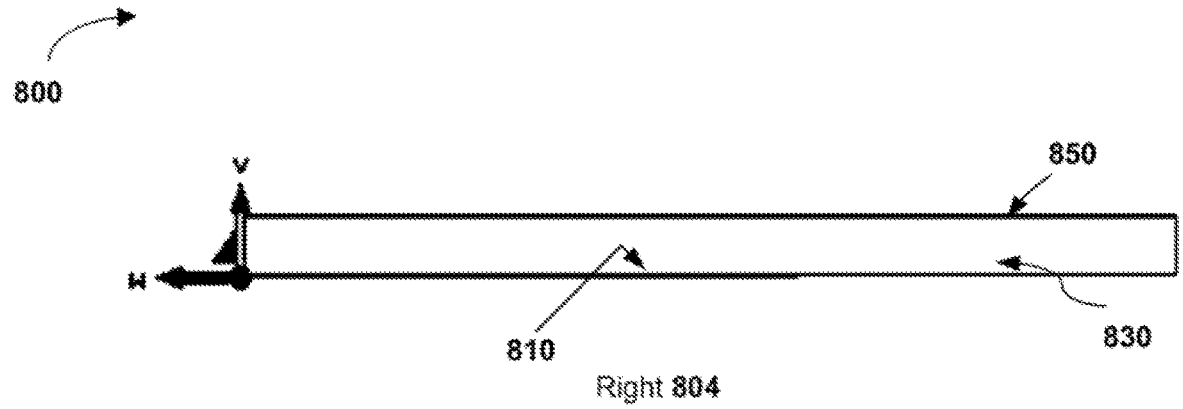
Right 804

SYSTEMS AND METHODS FOR MICROWAVE JAMMING OF MOLECULAR RECOGNITION

CROSS-REFERENCE TO RELATED APPLICATIONS

This application is a US National Stage of International Application No. PCT/US2013/026193, filed 14 Feb. 2013, which claims the benefit of U.S. Provisional Application No. 61/598,675, filed 14 Feb. 2012, each herein fully incorporated by reference.

BACKGROUND

The mechanism behind microwave spectroscopy is rooted in quantum mechanics, but can be understood from a classical perspective. For a molecule to exhibit a microwave spectrum it must have one or more dipole moments. In the presence of an electromagnetic wave the dipoles will be driven, resulting in the rotation of the molecule. The ubiquitous microwave oven is a kitchen appliance based on this principle. The electromagnetic field generated by the magnetron in the microwave oven induces the rotation of the H2O molecules in the food and this rotation results in a transfer of heat to the region surrounding each H2O molecule.

Microwave spectroscopy has been used as a means of identifying molecular content of far away planets. For example, the microwave spectra emitted by the molecules in the gaseous clouds of Jupiter are measured via radio telescopes on earth. The collected spectra are then analyzed and compared with the spectra of molecules measured in laboratories. Recently, there has been considerable work in identifying the microwave spectra of biologically relevant molecules such as DNA.

Another developing technological field is quorum sensing. As an evolutionary predecessor to the endocrine system, microbes communicate with one another by sending out small molecules. When these molecules are received by the other microbes in the community they trigger gene expression. For example, for a colony of *Pseudomonas aeruginosa* bacteria, the 3-oxo-C12 AHL (“C12”) molecule signals that a bio-film should be constructed, in essence, a protective dome over the colony that can block chemical treatment.

So-called quorum-quenching mechanisms are currently being explored so as to minimize bio-film formation by microbes such as *P. aeruginosa*. Conventional approaches have been limited to antibodies which bind up the C12 molecules or drugs which are intended to do the same. However, these conventional treatments are unable to pass through an established bio-film. Moreover, drug treatments can have deleterious side effects and undesirable systemic impact.

SUMMARY

Some or all of the above deficiencies may be addressed by certain implementations of the disclosed technology. Certain implementations include directing limited frequencies of microwave signals toward a target molecule, driving a motion of the target molecule to impact molecular recognition. For example, in some implementations, microwave signals can be used to impede the binding of the quorum sensing C12 molecule by receptors of *P. aeruginosa*. The relatively harmless energy levels for the prescribed microwave energy and the specificity of the microwave frequencies involved localize impact and reduce the risk of side effects.

According to an example implementation, a method for generating a microwave biological control signal is provided. The method can include obtaining a microwave spectrum associated with the rotational modes of a molecule. From one or more peaks in the spectrum, a mode of molecular movement can be identified. Then a microwave signal profile can be generated for driving a motion of one or more binding portions of the molecule associated with the identified mode. In a further implementation, microwave signals can be generated based on the signal profile. In another further implementation, the microwave signals can be output by one or more antennas. The method can also include identifying a molecule associated with a biological event.

According to an example implementation, system for generating a microwave control signal is provided. The system can include a processor and a memory operatively coupled to the processor. The memory can be configured for storing instructions that, when executed by the processor, cause the system to receive a microwave spectrum associated with rotational modes of a molecule, identify a mode of molecular movement associated with one or more peaks in the spectrum, and generate, by the processor, a microwave signal profile based on the identified mode for driving a motion of the molecule.

According to an example implementation, a computer-readable medium containing instructions that, when executed by at least one processor in a system, cause the system to perform a method including, receiving a microwave spectrum associated with the rotational modes of a molecule. From one or more peaks in the spectrum, a mode of molecular movement can be identified. Then a microwave signal profile can be generated for driving a motion of one or more binding portions of the molecule associated with the identified mode. In a further implementation, microwave signals can be generated based on the signal profile. In another further implementation, the microwave signals can be output by one or more antennas.

Other implementations, features, and aspects of the disclosed technology are described in detail herein and are considered a part of the claimed disclosed technology. Other implementations, features, and aspects may be understood with reference to the following detailed description, accompanying drawings, and claims.

BRIEF DESCRIPTION OF THE FIGURES

Reference will now be made to the accompanying figures and flow diagrams, which are not necessarily drawn to scale, and wherein:

FIG. 1 depicts an illustration of a block diagram of the system, according to an example implementation.

FIG. 2A-B depict illustrations of the quorum sensing molecule, according to an example implementation.

FIG. 3 depicts an illustration of the rotational spectrum, according to an example implementation.

FIG. 4 depicts an illustration of a flow diagram of the method, according to an example implementation.

FIG. 5 depicts an illustration of a flow diagram of the method, according to an example implementation.

FIG. 6 depicts an illustration of a block diagram of the computing device system architecture, according to an example implementation.

FIG. 7A depicts an illustration of front, back, left, and right views of the linearly polarized patch antenna, according to an example implementation.

FIG. 8A depicts an illustration of front, back, left, and right views of the circularly polarized patch antenna, according to an example implementation.

DETAILED DESCRIPTION

Figure 1:
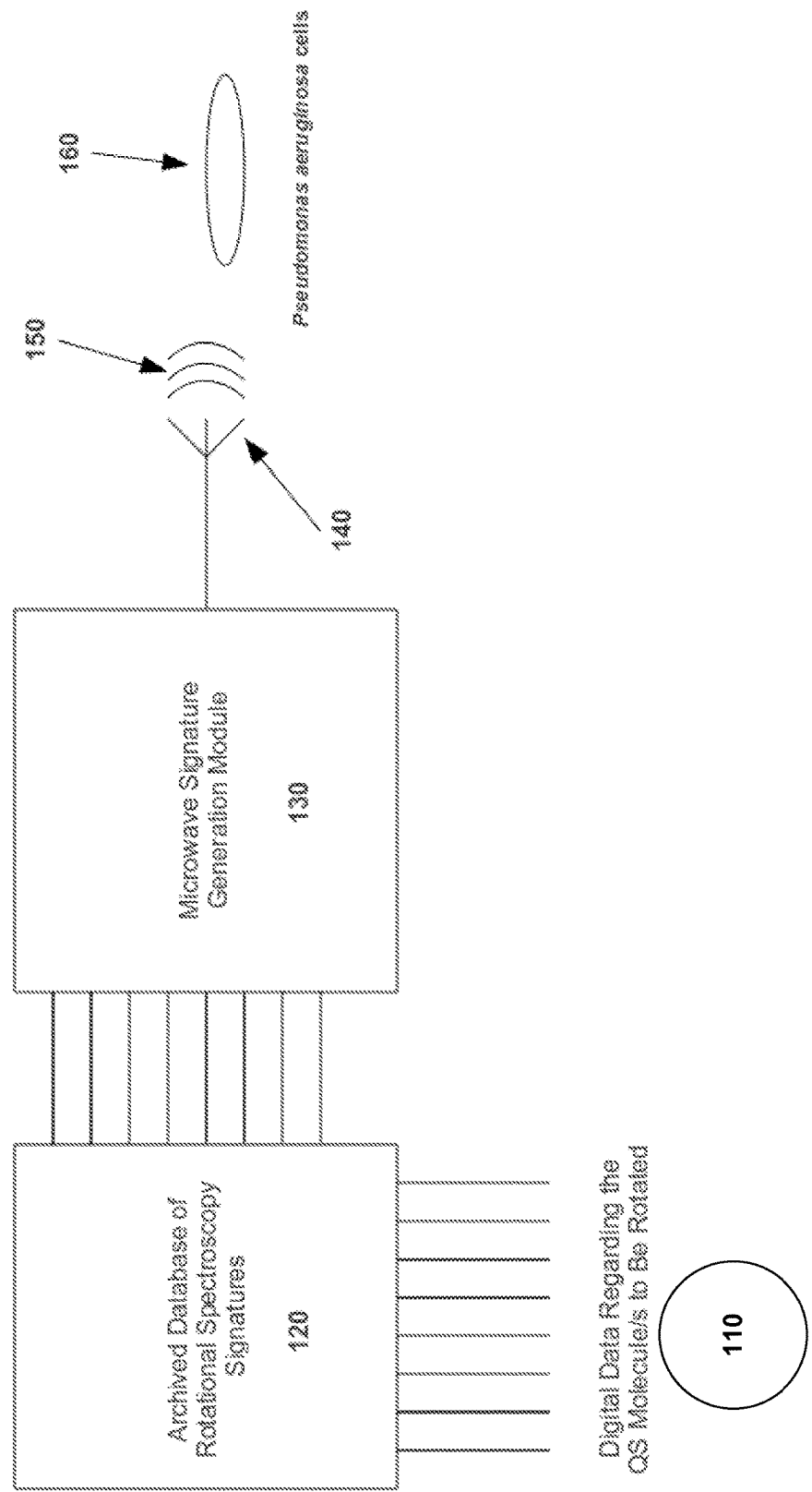

The disclosed technology is based upon a radical concept—that a microwave signal of the proper frequency and character (e.g., polarization, temporal characteristics) can be used to alter the nature of biomolecular interactions.

In certain implementations, these microwave signals can cause target molecules to rotate billions of times per second and thus impede their binding. Such impedance will herein be referred to as microwave jamming, as in essence, certain implementations can provide a microwave signal which will jam cell-to-cell communication in an analogous fashion to which radar signals are jammed in electronic warfare. By jamming the microbe-to-microbe communication, certain implementations of the disclosed technology can impede the formation of bio-film by *P. aeruginosa*.

In describing example implementations, additional terminology will be resorted to for the sake of clarity. It is not intended that the disclosed technology be limited in scope to the details of construction and arrangement of components set forth in the following description or illustrated in the drawings. Rather, the disclosed technology is capable of other implementations and of being practiced or carried out in various ways.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. Relational terms such as "first" and "second," and the like may be used solely to distinguish one entity or action from another entity or action without necessarily requiring or implying any actual such relationship or order between such entities or actions. The term "or" is intended to mean an inclusive "or." Further, the terms "a," "an," and "the" are intended to mean one or more unless specified otherwise or clear from the context to be directed to a singular form. The term "include" and its various forms are intended to mean including but not limited to.

*Pseudomonas aeruginosa* is a life-shortening infection in the lungs of patients with Cystic Fibrosis (CF). *P. aeruginosa* sets up residence in healthy lungs as well as CF lungs. In CF patients, however, a genetic defect inhibits the body's ability to fight off the infection. Quorum sensing molecules transmitted between members of the microbial community are an indicator of what the microbes are up to. From a biological point of view, the quorum sensing molecules control gene regulation and inform the colony when to, among other things, replicate, sporulate, and when to construct a protective bio-film. Once the protective bio-film has been constructed, chemical treatment is unlikely to be effective in managing *P. aeruginosa* colonies.

At present there is considerable interest in the field of controlling bacterial infections by quenching their quorum sensing systems. Problematic in these approaches is the fact that conventional attempts to quench the quorum sensing systems involve chemical means. These techniques are futile once a biofilm has been constructed.

Certain implementations of the disclosed molecular jamming techniques can be effective against even microbial colonies with established bio-films. Although chemicals may not penetrate a bio-film, microwave energy can. For example, a typical bio-film thickness can be approximately 100 μm. Assuming the conductivity of the biofilm to be roughly equal to that of seawater, at 10 GHz, an example electromagnetic signal may be reduced by only 0.073 dB in propagating through the bio-film. Moreover, as certain implementations include placing a microwave antenna in close proximity to the offending microbial colony, there can be very little loss of electromagnetic energy during propagation through the bio-film.

Virtually every biomolecular interaction involves molecular recognition as a critical component—disrupt molecular recognition and a cell process has been altered or stopped. Although this description details an exemplary application of microwave jamming for inhibiting bio-film formation among *P. aeruginosa* colonies, the techniques disclosed herein have a wide variety of applications.

For example, and not limitation, certain implementations of the disclosed technology can be applied to mold treatment. Currently, the accepted method for eradicating mold from a home is to use chemicals to kill the microbial communities associated with the mold. Using the disclosed technology, microwave energy can be transmitted at the proper frequency to jam the communication within the mold microbial community and ultimately resulting in cell death.

Another potential application is the supplement or replacement of herbicides and insecticides with microwave jamming. In an example implementation, rather than genetically engineer plants, such as soy beans, to be unaffected by highly toxic herbicides, non-genetically engineered soy beans could be planted and microwave transmitters placed in the crop field with the soy beans. In another example implementation, an unmanned air vehicle (UAV) equipped with a microwave transmitter over the field. In this example implementation and others, alternate means of radiation delivery will be apparent to one of skill in the art.

Yet another potential application of this technology is for use in cancer treatment. In an example implementation, a microwave signal or sequence of signals can be targeted at cancer cell DNA. Sustained rotational stressing on the DNA from the microwave energy can cause the cancer cell's DNA to fracture, similar to the mechanism behind some chemotherapy drugs. For localized treatment, an antenna on a catheter can be fed to a location near the tumor and the microwave signal transmitted for sufficiently long to weaken or kill the cancer cells. Because microwave energy at certain frequencies (e.g. 10 GHz) will not propagate very far in tissue, the microwave jamming signal is likely to destroy the tumor with reduced or nominal collateral damage to healthy surrounding tissue. In another example implementation, targeted microwave radiation can be used to block cell-to-cell communication for angiogenesis.

Other and additional applications of the disclosed technology are contemplated and within the scope of this disclosure.

Referring now to the figures, in which like reference numerals represent like parts throughout the views, various implementations of the disclosed technology will be described in detail.

Figure 3:
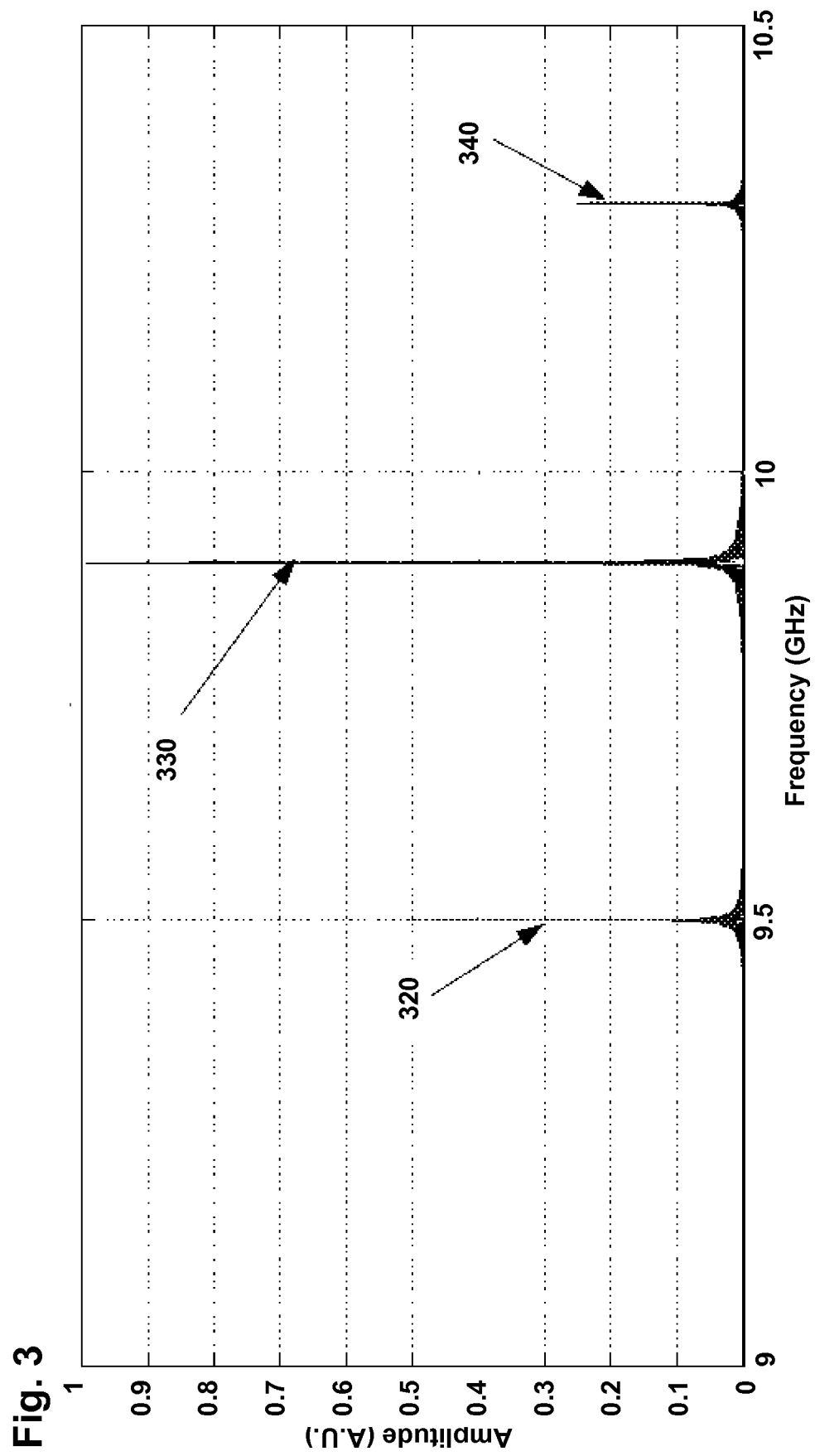
Figure 4:
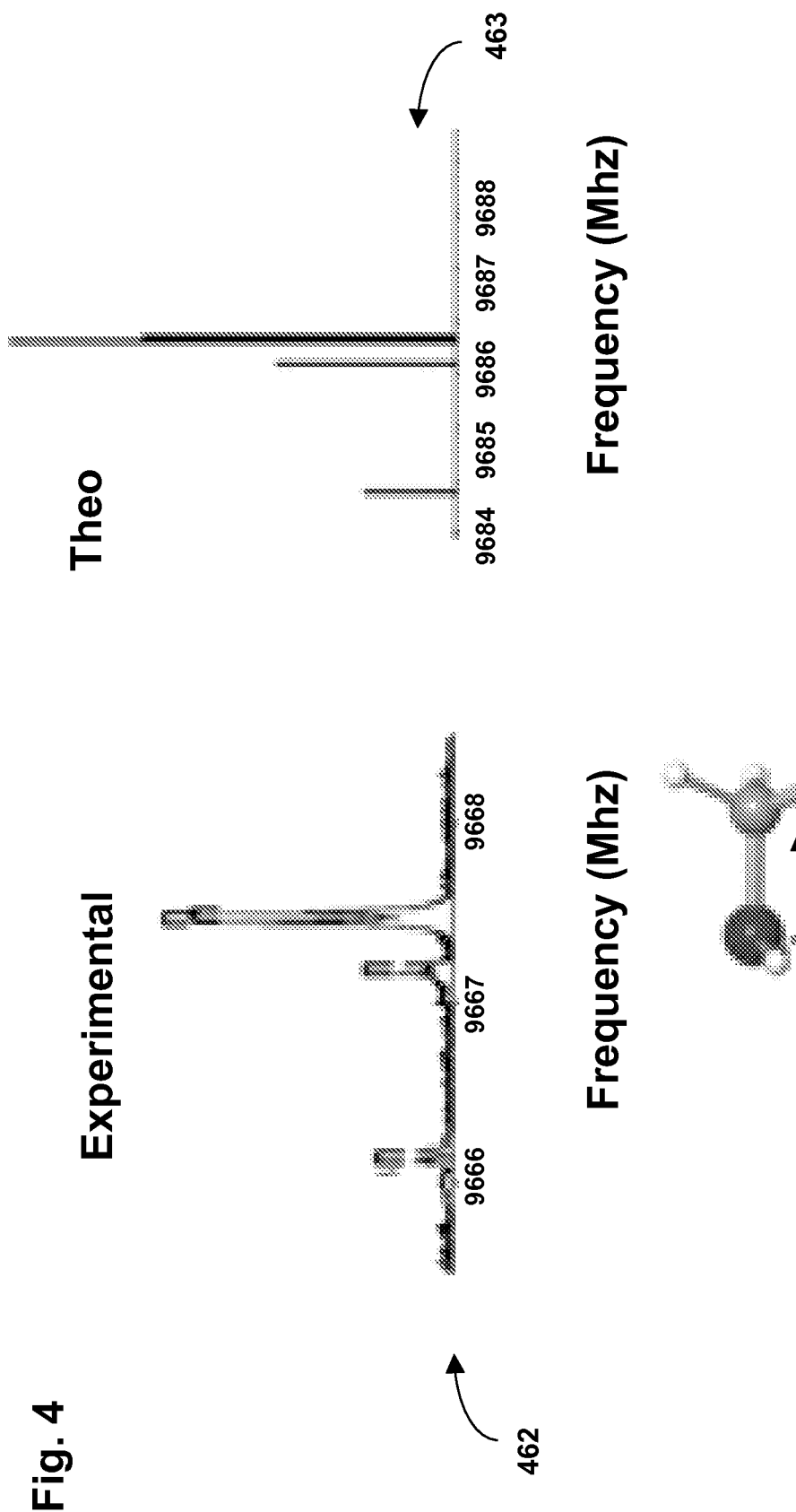
Figure 4:
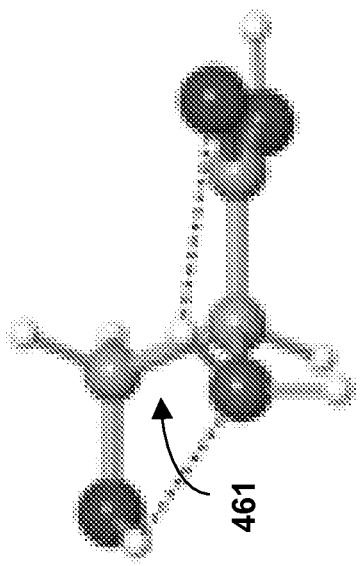
Figure 5:
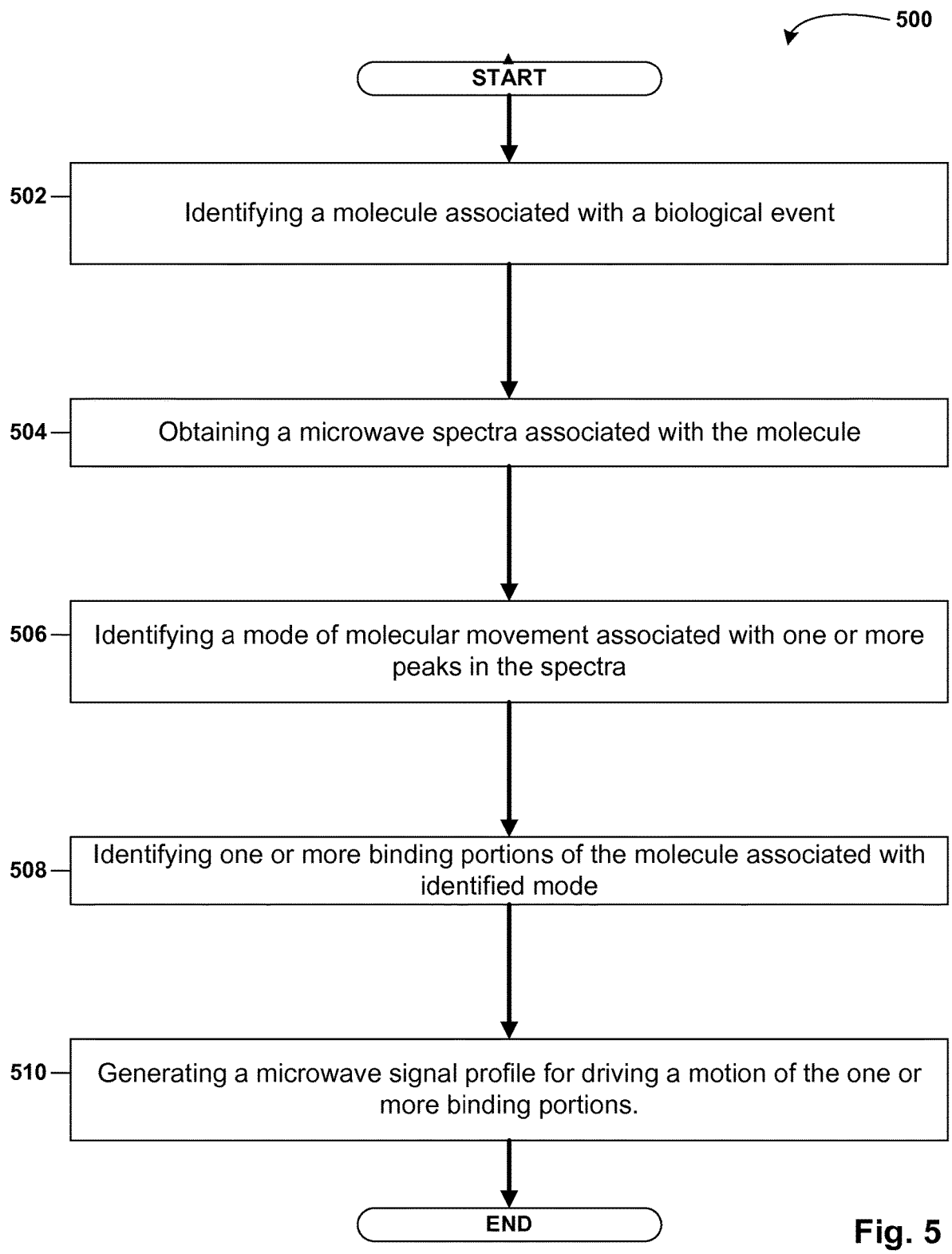

In an example implementation, the disclosed technology can be used to treat infections of *P. aeruginosa*. FIG. 1 depicts an illustration of a block diagram of the system, according to an example implementation. As shown in FIG. 1, a digital encoding 110 of the quorum sensing molecule C12 can be input to a database of rotational spectroscopy signatures 120 to obtain the appropriate microwave spectra. The signature retrieved from the database can be sent to the Microwave Signature Generation Module (MSGM) 130. The output of the MSGM can drive an antenna 140 for outputting microwave signals.

Electromagnetic waves 150 output by the antenna 140 can propagate towards the colony of *P. aeruginosa* cells 160, causing the C12 molecules within the colony to rotate at the frequencies of the microwave signal. Accordingly, a microwave signal in the GHz range can cause a molecule to rotate billions of times per second, thus impeding molecular recognition and blocking the message to form a bio-film. In a further implementation, a CF patient could be treated using a catheter containing the antenna. The catheter could be threaded into the lungs and positioned proximal to the location of the infection.

Microwave jamming of the quorum sensing communication system can be used in conjunction with conventional treatments unable to penetrate the bio-film such as antibiotics. Moreover, in some implementations, microwave jamming of cell-to-cell communication can lead directly to cell death. Thus, certain implementations of the disclosed technology can provide a treatment methodology which requires no drugs—only microwave energy of the correct frequencies—ushering a new class of targeted microwave pharmaceuticals.

Certain implementations of the disclosed technology are generally applicable to moderating molecular recognition in any biological interaction. FIG. 5 depicts an illustration of a flow diagram of the method, according to an example implementation. The method 500 starts in block 502, and according to an example implementation, includes identifying a molecule associated with a biological event. The biological event can be any event in which molecular recognition, i.e., binding of the molecule, is implicated. For example, the biological event could include conversion of a substrate or the reuptake of a neurotransmitter. Moreover, the biological event can be a complex or multi-stage process involving the binding of several molecules, as in angiogenesis or apoptosis.

In certain implementations, the target molecule can be a quorum sensing molecule, such as C12 for instructing *P. aeruginosa* communities to form a bio-film, or any of various other molecules biologically interactive molecules, including, without limitation, ligands, substrates, hormones, neurotransmitters, cytokines, growth factors, toxins, sugars, etc. Moreover, in some implementations, the target molecule may moderate molecular recognition of a second molecule, for example, as with an enzyme inhibitor or activator.

Target molecules exhibiting one or more dipole moments can effectively respond to the microwave signals. For example, polar molecules have a permanent dipole moment, and thus can be suitable targets for implementations of the disclosed technology. However, in certain implementations, a dipole moment can be induced in a molecule that would otherwise be unresponsive to targeted microwave signals, for example by application of an electric field.

FIGS. 2A-B depict illustrations of the quorum sensing molecule, C12 200, according to an example implementation. As shown in FIG. 2A, the elements hydrogen (H) 220, oxygen (O) 230, nitrogen (N) 240, and carbon (C) 250 are represented by spheres of various sizes. In this molecule, the presence of the uneven charge distribution of the electron clouds leads to a net dipole moment 260. There are other weaker dipole moments in the molecule related to the hydrogen bonding between the H atoms and the N and O atoms. The complexity of these dipoles and attendant quadrupole, as well as the molecule's moment of inertia tensor gives rise to the rich microwave spectra which can be specific to a particular conformer of a molecule.

In block 504, the method 500 includes obtaining a microwave spectra associated with the rotational modes of the molecule. These spectral frequencies can be very narrow in bandwidth. Thus, the identification of the rotational resonances can help ensure that the microwave energy to be radiated into a targeted collection of cells will substantially affect only the targeted molecule of interest.

In certain implementations, the microwave spectra can be measured, using, for example, microwave spectroscopy. For astronomical spectroscopic studies, the thermal motion of the molecules in a gas leads to rotation of these molecules which in turn generates the microwave spectra observed. In microwave spectroscopic techniques such as laser ablation-molecular beam Fourier Transform microwave (LA-MB-FTMW) spectroscopy, attenuation of specific frequencies is looked for through a carefully constructed gas of the target molecule surrounded by a select number of H2O molecules.

In another implementation, spectra can be obtained by modeling the molecule and analytically deriving the spectra. These calculations can consider the molecule of interest, e.g. C12, with the proper number of H2O molecules which will surround it in its biological environment. The modeled spectra can closely approximate experimentally measured spectra in some cases. For example, FIG. 4 depicts an illustration of an experimentally measured spectrum 462 and theoretically derived spectrum 463 for a an example serine conformer 461. There are a host of preexisting programs that can be used to predict the rotational resonances of a molecule, for example, the open source program, GAMESS, and the commercially available program, Gaussian09.

In certain implementations, an indication or signature of the spectra can be stored in or retrieved from a database. Accordingly, a previously measured or derived spectra for the target molecule can be obtained from the database, obviating the need to re-analyze the rotational spectra of the target molecule for each treatment session. For example, as shown in FIG. 1, a digital encoding 110 of the target molecule can be generated and input to an archived database of rotational spectroscopy signatures 120. The database can provide the rotational spectra for the target molecule, in accordance with block 504.

FIG. 3 depicts an illustration of the rotational spectra 300 for C12, according to an example implementation. As shown in FIG. 3, the rotational frequencies of these example spectra are illustrated by the peaks 320, 330 and 340. These frequency ranges corresponding to these peaks can be substantially unique to the target molecule—so much so that different conformers of the same molecule can have distinct spectra.

In this example, the rotational spectra appear sufficiently unique and narrow band that they can be used to discriminate between conformers of the same molecule. Accordingly, it is unlikely that this signal, which drives the rotational modes of the molecule C12, will cause other molecules to rotate. (However, a cautious approach could also consider the spectra of other molecules.) Moreover, microwave energy is strongly attenuated in organic tissue as, from an electromagnetic standpoint, tissue is very similar to sea water. Thus a catheter with an antenna for outputting targeted microwave signals that is introduced into the lungs of a CF patient may only affect the cells nearby. Hence, systemic effects can be reduced or minimized, in contrast to treatment with chemicals.

In block 506, the method 500 includes identifying a mode of molecular movement associated with one or more peaks in the spectra. In certain implementations, this can include relating one or more peaks in the spectra to a mode of vibration of one or more moieties, or functional groups, of the molecule. By driving the motion of moieties that include binding portions, the rate of binding of the target molecule can be affected. For example, certain implementations can drive the rotation of the molecule C12 by irradiating the sample with microwave energy at the appropriate frequencies gleaned from molecular modeling and an experimental technique, such as LA-MB-FTMW.

In certain implementations, the induced motion can impede the binding of the target molecule. However, targeted microwave signals can be designed to induce molecular motion to achieve other effects. In various other implementations, the induced motion can promote binding of the target molecule, promote unbinding of the molecule, or trigger release of the molecule, for example, from a receptor. In yet another implementation, the induced motion can cause the target molecule, itself, to fracture from physical stress.

In block 508, the method 500 includes identifying one or more binding portions associated with identified mode. In certain implementations, a binding portion can be all or a portion of an active site.

In block 510, the method 500 includes generating, using a processor, a microwave signal profile for driving a motion of the one or more binding portions. In certain implementations, one or more microwave signals can be generated based on the signal profile. In another implementation, the generated signal profile can be stored, for example, on a database for later retrieval and use.

In certain implementations, blocks 506 to 510 can be performed by the MSGM 130. In an example implementation, the MSGM can select a subset of the rotational spectroscopy signal which is most likely to be unique to the target molecule so as not to induce incidental rotation of other molecules. Moreover, the MSGM can prescribe other microwave signal characteristics to achieve the desired motion and corresponding effect. One of skill in the art will be able to select microwave signal characteristics for achieving the desired effect.

For example, a basic microwave signal profile may prescribe outputting a fixed frequency microwave signal within a range corresponding to the one or more peaks in the rotational spectra. However, in some implementations, a more complicated signal profile can be used to exert greater control over the motion of a target molecule. In certain implementations, a microwave signal can be output that sweeps or chirps between frequencies within a frequency range corresponding to the one or more peaks of the spectra. In another example implementation, the frequency of the first microwave signal can "hop" between frequency ranges corresponding to the first peak and the second peak.

According to another example implementation, the microwave signal can be a substantially continuous signal. In another implementation, the microwave signal can be a discrete or pulsed signal.

According to another example implementation, the microwave signal can have a substantially narrow bandwidth, for example less than about 100 MHz. Narrowing the bandwidth can reduce side effects by reducing the possibility of exciting molecules other than the target molecule. In another implementation, the bandwidth of the microwave signal can be constrained so as not overlap frequency ranges corresponding to more than one peak of the associated spectra.

According to another example implementation, the amount of power of the microwave signal can be less than a microwatt. However, especially if significant attenuation is expected, the power may be increased such that the power received at the target molecule meets a certain threshold. In one implementation, the total amount of power of all microwave signals output can be less than a microwatt.

According to another example implementation, a microwave signal profile can prescribe outputting multiple microwave signals of the various qualities described above. In one implementation, the microwave signals can be a sequence of microwave signals. In another implementation, the microwave signals can be output concurrently.

In certain implementations, the generated microwave signals 150 can be output from one or more antennas 140. The antennas can be designed and uniquely constructed for the frequency range of the desired rotational spectra and for efficiency in near-field generation. Moreover, the antennas can be constructed to emanate radiation with one or more of elliptical, linear, or circular polarizations. One of skill in the art will be able to select antenna properties to achieve the desired effect.

According to an example implementation, the antenna can be placed inside a catheter or similar device. The catheter can be placed inside a patient substantially proximal to a microbial infection or potential infection site. For example, a catheter could be threaded into the lungs of a CF patient. In another example implementation, the antenna can be placed in a sleeve, patch, or other suitable construct for placement or attachment substantially adjacent to the skin of a patient. For example, the antenna could be placed next to a burn site on a patient to manage infection. In another example implementation, a device containing the antenna could be surgically implanted, and coupled to an internal or external signal generation means. In yet another example implementation, a device containing the antenna could be ingested. Moreover, in another example implementation, the antenna could be incorporated into a device for cleansing. For example, targeted microwaves could be used to manage bio-film formation on contact lenses or other medical devices.

Two example antennas were designed and constructed to output radiation at 10.2 GHz, one of the important frequencies in the rotational spectra of C12, as shown in FIG. 3. The antennas were of two types, linearly polarized and circularly polarized antenna. The two example antennas are now described in detail.

Figure 7B:
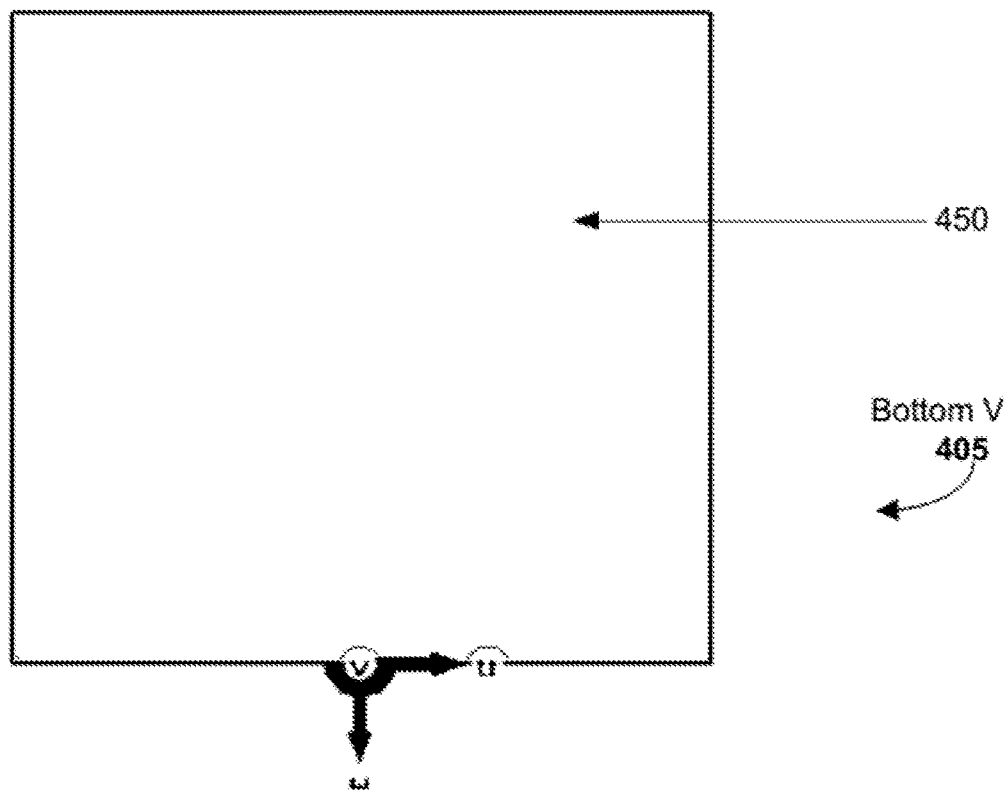
FIG. 7B depicts an illustration of top and bottom views of the linearly polarized patch antenna, according to an example implementation.
Figure 7B:
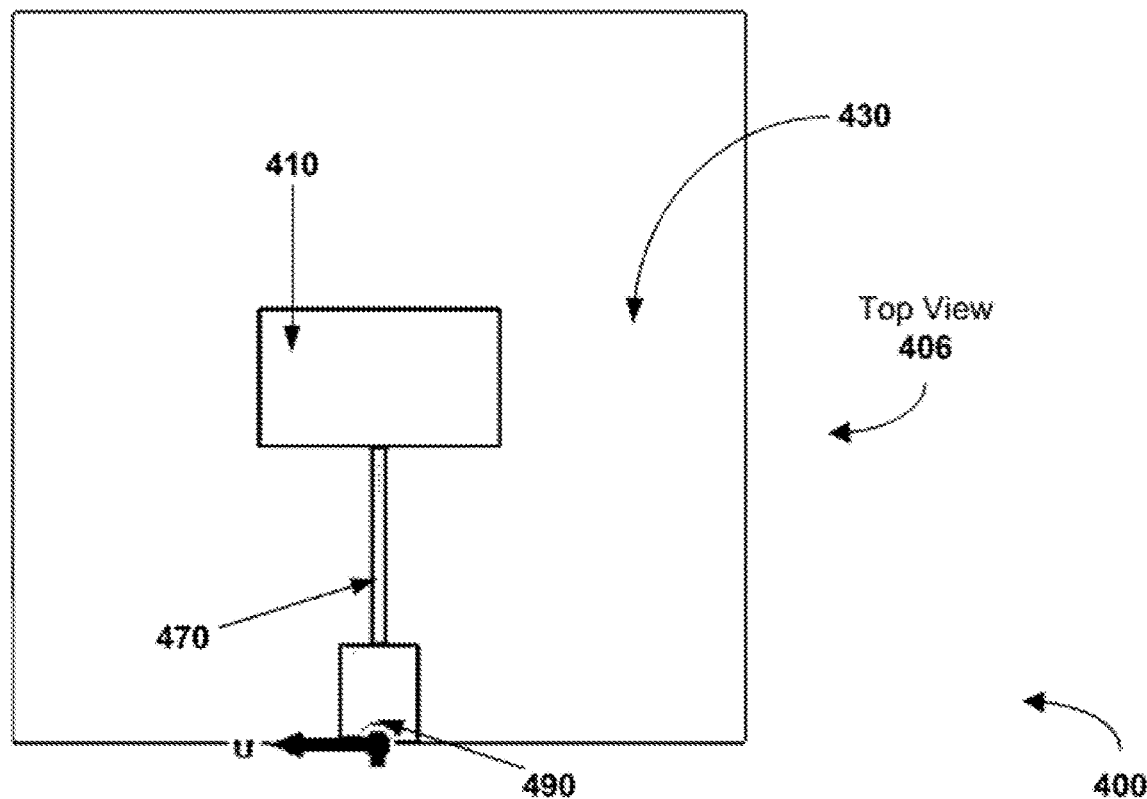

A single-element linearly polarized 10.2 GHz antenna 400 was designed to create a template antenna that could be phased to produce a high-gain antenna. FIGS. 7A and 7B depict illustrations of front 401 back 402 left 403 right 404 bottom and top views of the linearly polarized antenna 400, according to an example implementation. The example antenna as shown in FIGS. 7A and 7B can be used as a building-block to create 2-element, 8-element, and 16-element antenna arrays. The antenna arrays can be phased a half-wavelength apart to provide for constructive interference. This constructive interference can provide radiation with greater intensity. If the radiation intensity is too low with the 1-element array, higher-element arrays can be used to provide greater exposure to 10.2 GHz radiation.

The example linearly polarized antenna 400 is a 10.2 GHz microstrip patch antenna. The patch 410 is 5.10 mm in length and 9.03 mm in width. The substrate 430 height is 1.524 mm and is made of FR4 substrate which has a relative permittivity of 4.3. The impedance of the antenna 400 is approximately 238.5 ohms. In order to match the antenna 470 400 to a 50 ohm transmission line 490, a quarter wave transformer 470 was used. The quarter wave transformer 470 has a length of 7.35 mm and a width of 0.535 mm. The 0.535 mm width gives the quarter wave transformer an impedance of ~109 ohms. A 50 ohm microstrip transmission line 490 is connected to the 109 ohm quarter wave transformer 470. The 50 ohm microstrip 490 line has a width of 2.97 mm and a length of 4.0 mm. Table 1 lists additional dimensions and specifications of the example linearly polarized antenna 400.

Figure 7C:
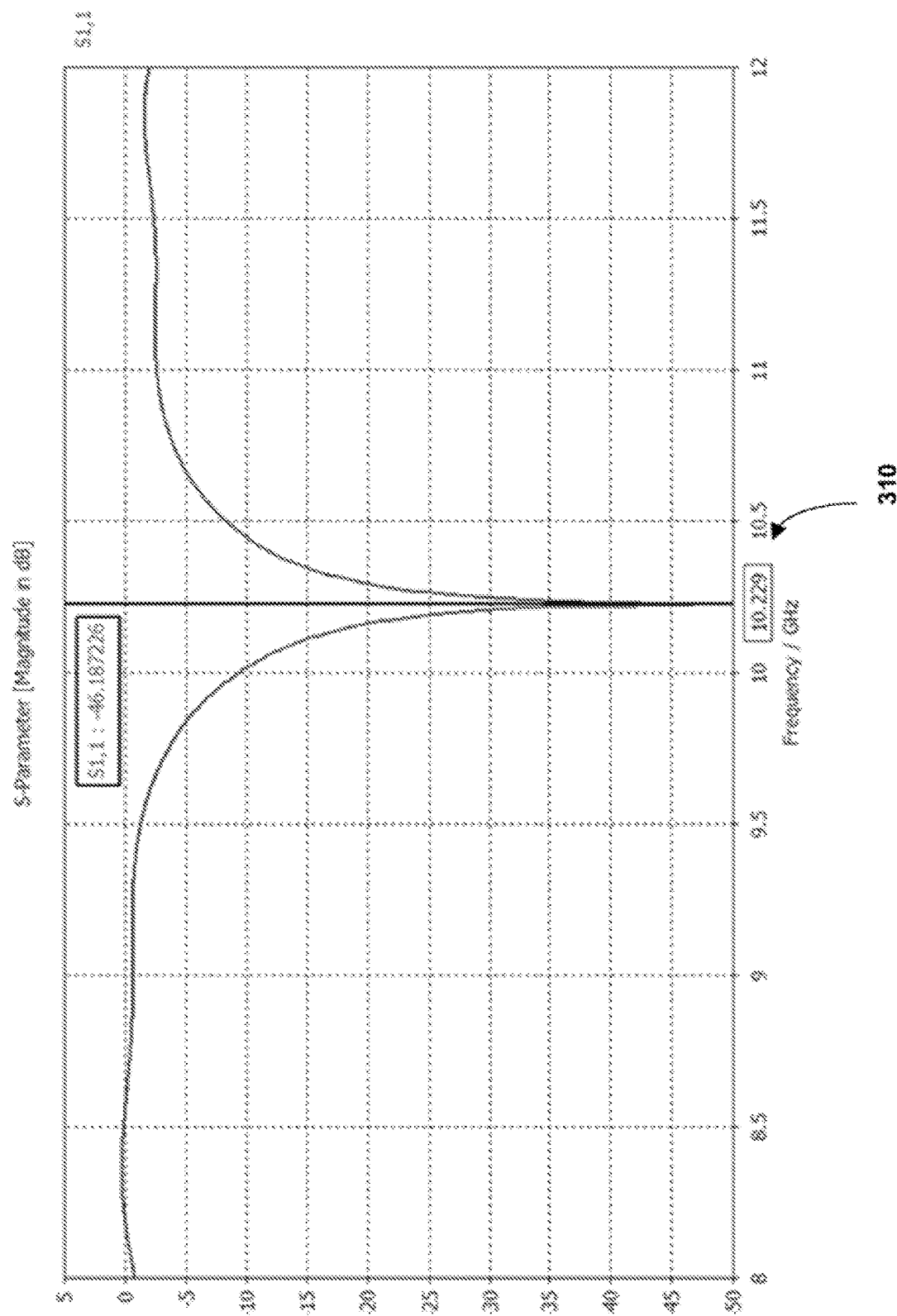
FIG. 7C depicts an illustration of a plot of S11 parameters for the linearly polarized patch antenna, according to an example implementation.

The connection of the patch 410, 109 ohm transmission line, and 50 ohm transmission line 490 is relatively reflection-less at 10.2 GHz, as illustrated in the S11 graphed in FIG. 7C. As shown in FIG. 7C, the antenna 400 is resonant at 10.229 GHz 310 and has a usable frequency range of approximately 9.7 GHz to 10.7 GHz.

Figure 7D:
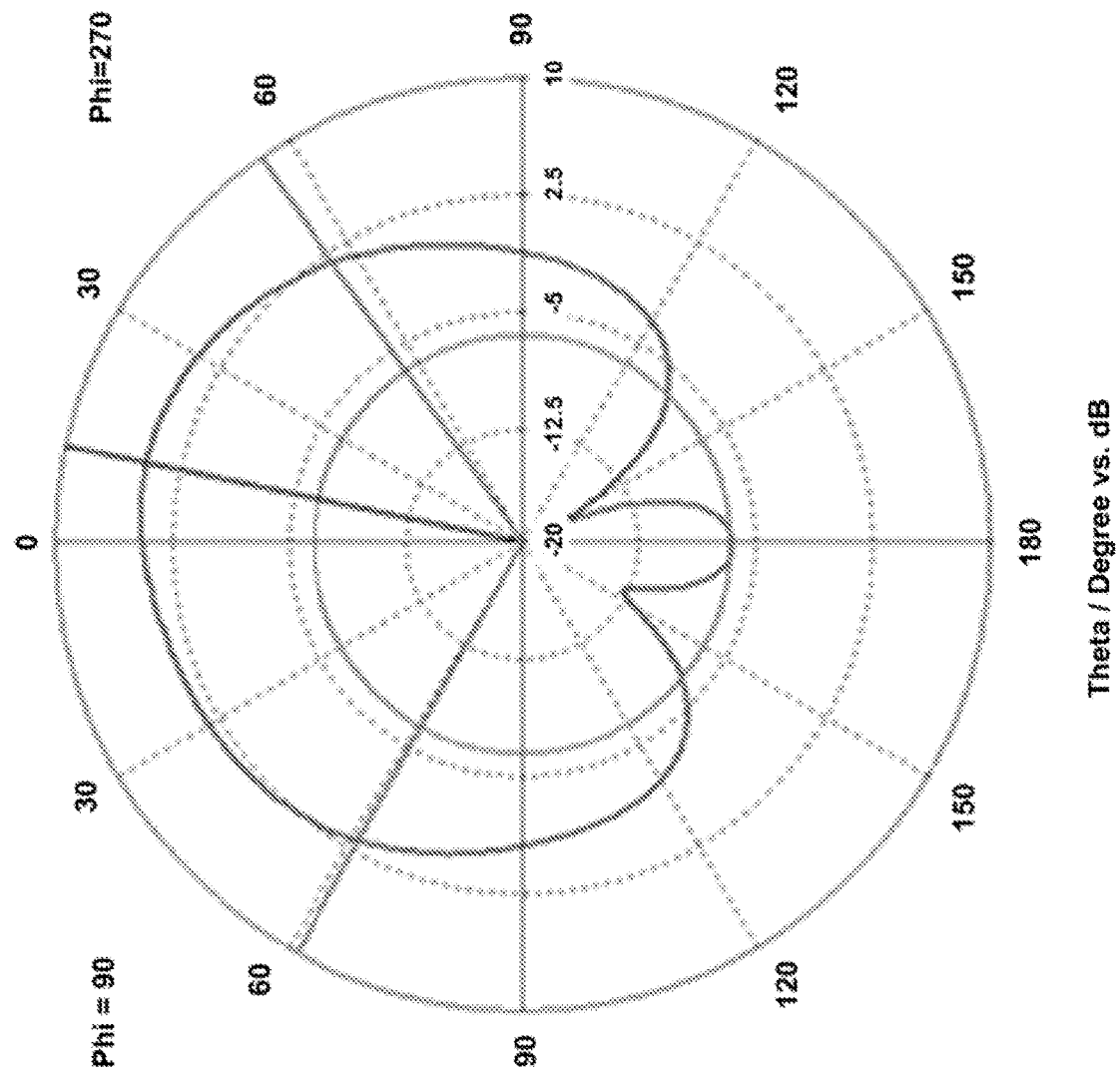
FIG. 7D depicts an illustration of a plot of realized gain for the linearly polarized antenna, according to an example implementation.

FIG. 7D depicts an illustration of a plot of realized gain for the linearly polarized antenna 400, according to an example implementation. FIG. 7D shows the azimuthal farfield realized gain pattern for the antenna. The antenna 400 has a realized gain of 5.1 dBi at 10.2 GHz.

TABLE 1

Dimensions of the 10.2 GHz 1-element Patch Antenna 400

| Reference | Parameter | Value |
|---|---|---|
| 410 | Patch | |
| | Patch Length | 5.10 mm |
| | Patch Width | 9.03 mm |
| | Patch Thickness | .038 mm |
| | Patch Material | Copper |
| 430 | Substrate | |
| | Substrate Thickness | 1.524 mm |
| | Substrate Width | 13.55 mm |
| | Substrate Length | 13.55 mm |
| | Substrate Relative Permittivity | 4.3 |
| 450 | Ground Plane | |
| | Ground Plane Length | 13.55 mm |
| | Ground Plane Width | 13.55 mm |
| | Ground Plane Thickness | .038 mm |
| | Ground Plane Material | Copper |
| 470 | Quarter Wavelength Transformer | |
| | Quarter Wavelength Transformer Length | 7.35 mm |
| | Quarter Wavelength Transformer Width | .535 mm |
| | Quarter Wavelength Transformer Thickness | .038 mm |
| | Quarter Wavelength Transformer Material | Copper |

TABLE 1-continued

Dimensions of the 10.2 GHz 1-element Patch Antenna 400

| Reference | Parameter | Value |
|---|---|---|
| 490 | 50 Ohm Transmission Line | |
| | 50 Ohm Transmission Line Length | 4.0 mm |
| | 50 Ohm Transmission Line Width | 2.97 mm |
| | 50 Ohm Transmission Line Thickness | .038 mm |
| | 50 Ohm Transmission Line Material | Copper |

Figure 8B:
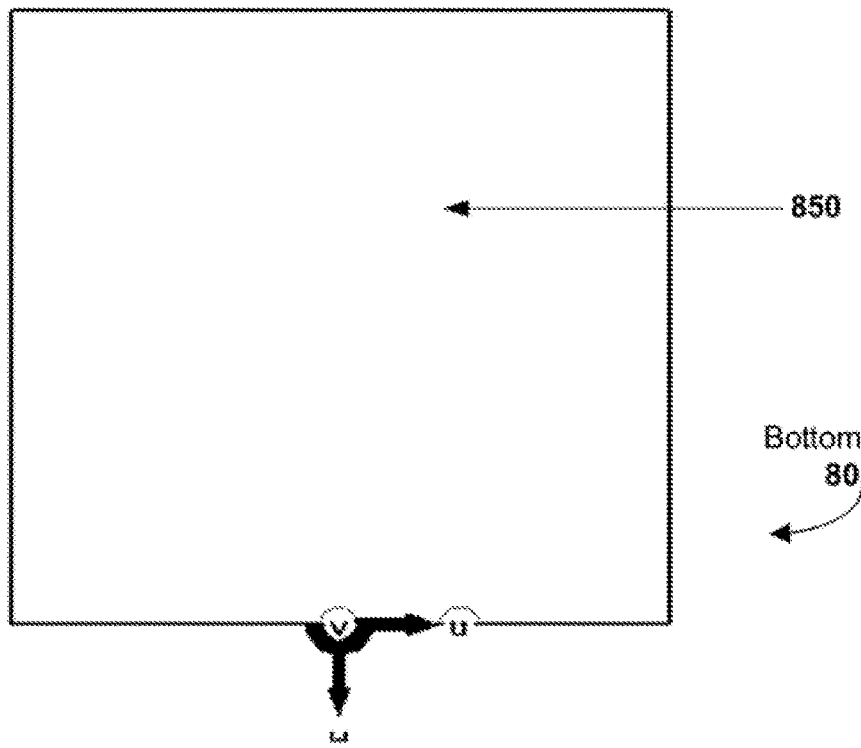
FIG. 8B depicts an illustration of top and bottom views of the circularly polarized patch antenna, according to an example implementation.
Figure 8B:
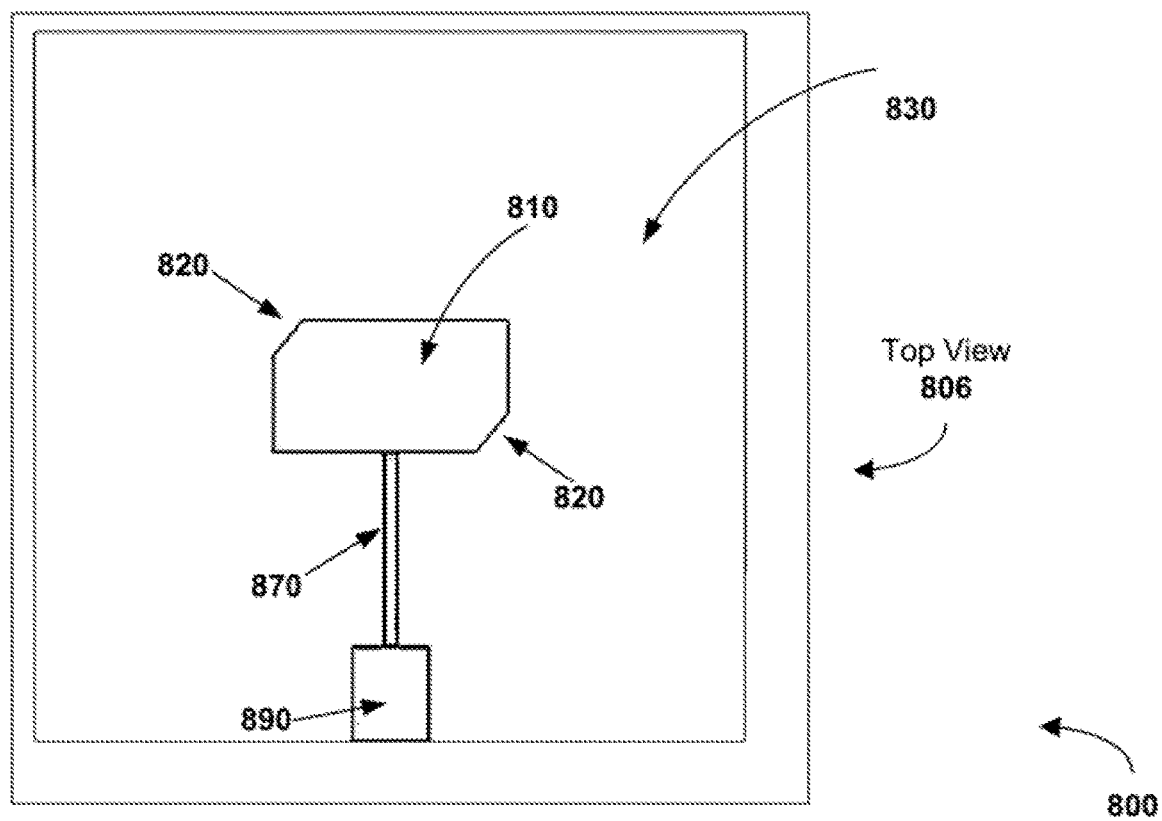

A circularly polarized patch antenna 800 was also designed and produced. FIGS. 8A and 8B depict illustrations of views of the circularly polarized antenna 800, according to an example implementation. One drawback of a linearly polarized antenna is in the linearity of is electric field. An electric field that is perpendicular to a molecule (or dipole moment) will not produce any induced EMF. In order to increase the induced EMF of the target molecule, a circularly polarized antenna 800 was designed. A circularly polarized antenna can create an electromagnetic field that has components in both the X direction and the Y direction, assuming the wave is travelling in the Z direction. Since the circularly polarized antenna contains equal E-field components in both the X and the Y direction, molecules that are possibly tangential to the X portion of the E-field will still be excited by Y-portion of the E-field. This notion can be of great importance when trying to excite molecules that are floating in an aqueous solution. The orientation of the molecules in the aqueous solution can be random. As such, using a circularly polarized electromagnetic field can raise the probability of exciting a molecule in the solution. The specifications for the 10.2 GHz circularly polarized antenna 800 are as follows:

The antenna 800 is a 10.2 GHz circularly polarized microstrip patch antenna. The patch 810 is 5.10 mm in length and 9.03 mm in width. The substrate 830 height is 1.524 mm and is made of FR4 substrate which has a relative permittivity of 4.3. There are cut-outs 820 in the upper left and bottom right corners. The cut-outs 820 are at approximately 45 degree angles to the corner and form a 45, 45, 90 degree triangle with side lengths of 1.12 mm. The cut-outs can create the circular polarizing experienced in the farfield radiation.

The impedance of the antenna 800 is approximately 238.5 ohms. In order to match the antenna to a 50 ohm transmission line 890, a quarter wave transformer 870 was used. The quarter wave transformer 870 has a length of 7.35 mm and a width of 0.535 mm. The 0.535 mm width gives the quarter wave transformer 870 an impedance of ~109 ohms. A 50 ohm microstrip transmission line 890 is connected to the 109 ohm quarter wave transformer. The 50 ohm microstrip line 89—has a width of 2.97 mm and a length of 4.0 mm. Table 2 lists additional dimensions and specifications of the example circularly polarized antenna.

Figure 8C:
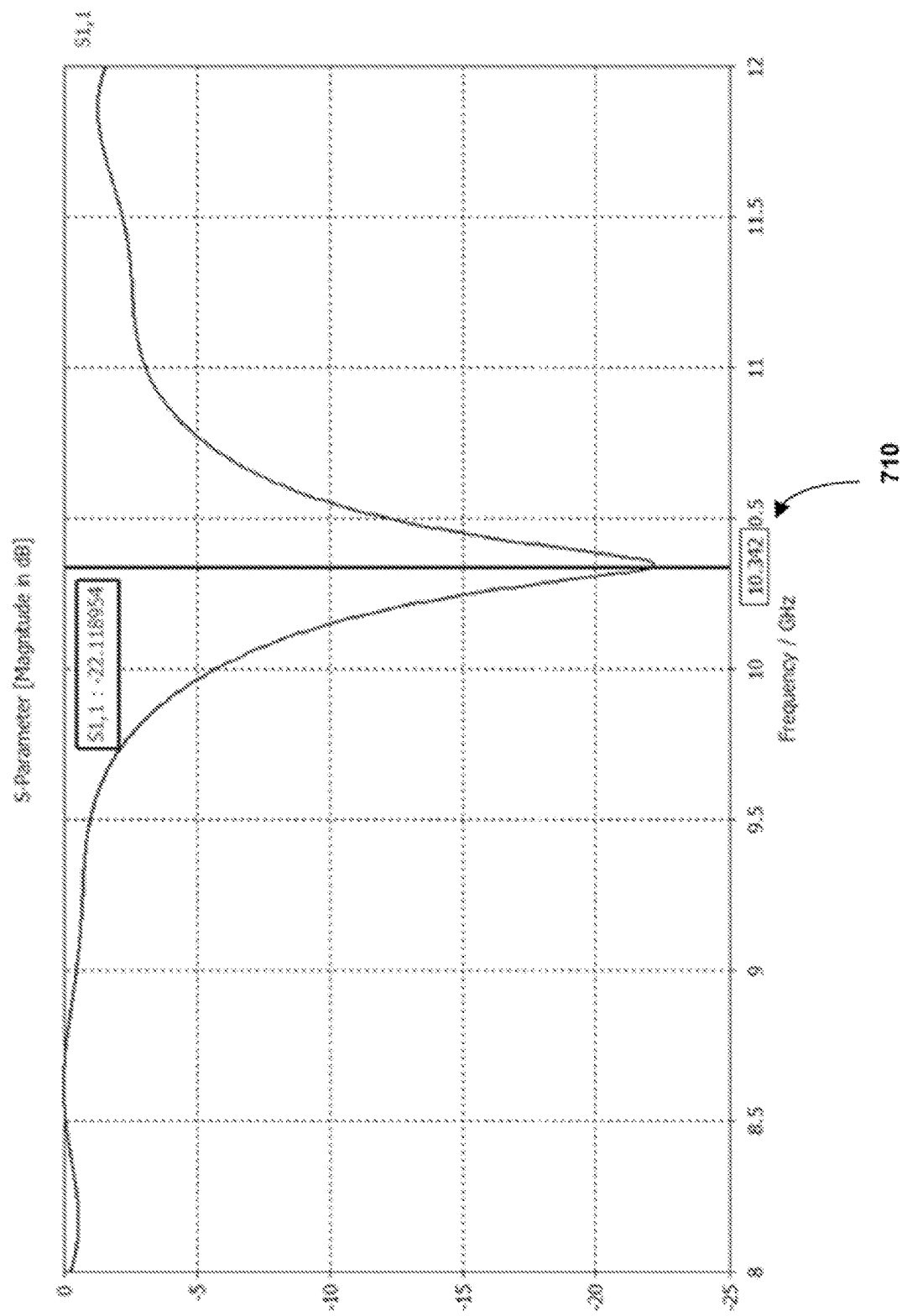
FIG. 8C depicts an illustration of a plot of S11 parameters for the circularly polarized patch antenna, according to an example implementation.

The connection of the patch 810, 109 ohm transmission line, and 50 ohm transmission line 890 is relatively reflection-less at 10.2 GHz. This notion is illustrated in the S11 graphed in FIG. 8C. FIG. 8C depicts an illustration of a plot of S11 parameters for the circularly polarized patch antenna, according to an example implementation. As shown in FIG. 8C, the example antenna is resonant at 10.342 GHz 710 and has a usable frequency range of approximately 10 GHz to 10.7 GHz.

Figure 8D:
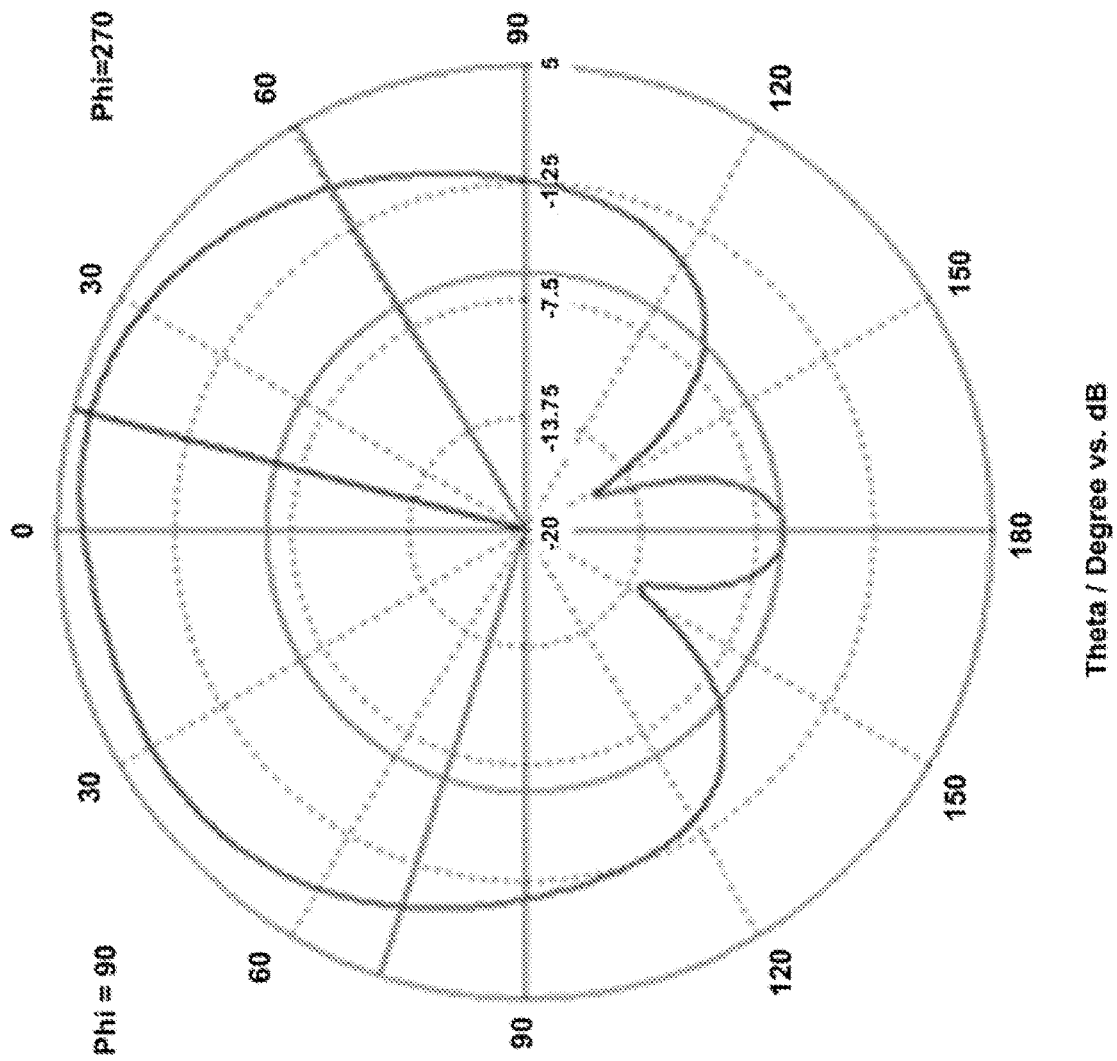
FIG. 8D depicts an illustration of a plot of realized gain for the circularly polarized antenna, according to an example implementation.

FIG. 8D depicts an illustration of a plot of realized gain for the circularly polarized antenna 800, according to an example implementation. FIG. 8D shows the azimuthal farfield realized gain pattern for the antenna. The antenna 800 has a realized gain of 4.1 dBi at 10.2 GHz.

TABLE 2

Dimensions of the 10.2 GHz Circularly Polarized Antenna 800

| Reference | Parameter | Value |
|---|---|---|
| 810 | Patch | |
| | Patch Length | 5.10 mm |
| | Patch Width | 9.03 mm |
| | Patch Thickness | .038 mm |
| | Patch Material | 45 degrees |
| 820 | Cut Out | |
| | Cut Out Width | 1.12 mm |
| | Cut Out Length | 1.12 mm |
| | Cut Out Angles | Copper |
| 830 | Substrate | |
| | Substrate Thickness | 1.524 mm |
| | Substrate Width | 13.55 mm |
| | Substrate Length | 13.55 mm |
| | Substrate Relative Permittivity | 4.3 |
| 850 | Ground Plane | |
| | Ground Plane Length | 13.55 mm |
| | Ground Plane Width | 13.55 mm |
| | Ground Plane Thickness | .038 mm |
| | Ground Plane Material | Copper |
| 870 | Quarter Wavelength Transformer | |
| | Quarter Wavelength Transformer Length | 7.35 mm |
| | Quarter Wavelength Transformer Width | .535 mm |
| | Quarter Wavelength Transformer Thickness | .038 mm |
| | Quarter Wavelength Transformer Material | Copper |
| 890 | 50 Ohm Transmission Line | |
| | 50 Ohm Transmission Line Length | 4.0 mm |
| | 50 Ohm Transmission Line Width | 2.97 mm |
| | 50 Ohm Transmission Line Thickness | .038 mm |
| | 50 Ohm Transmission Line Material | Copper |

Various implementations of the disclosed technology may be embodied all or in portion in non-transitory computer readable media for execution by a processor. An example implementation may be used in an application of a medical device, but other computing devices.

Figure 6:
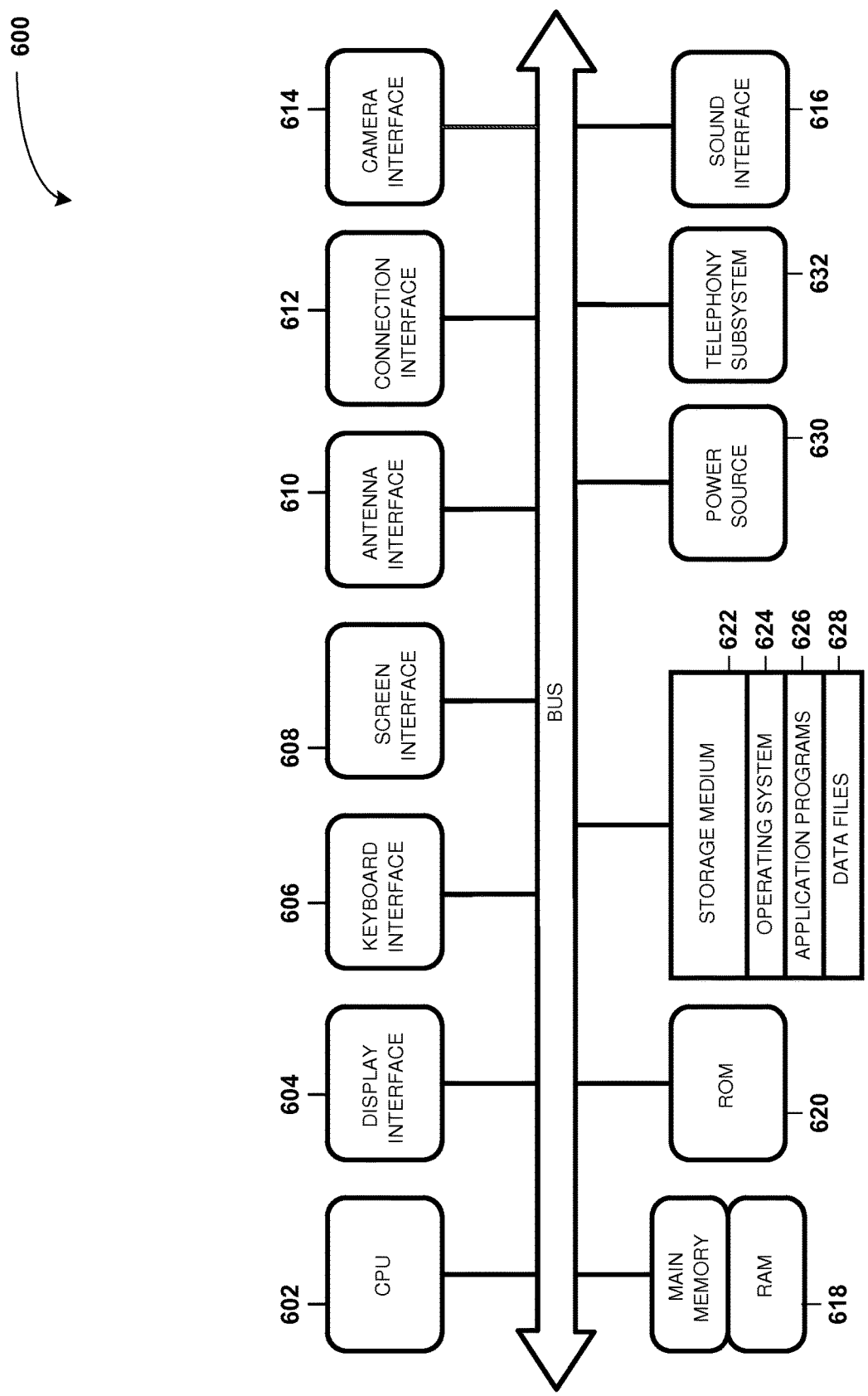

FIG. 6 depicts a block diagram of an illustrative computer system architecture 600 according to an example implementation. Certain aspects of FIG. 6 may be embodied in a computing device. It will be understood that the architecture 600 is provided for example purposes only and does not limit the scope of the various implementations of the communication systems and methods.

The architecture 600 of FIG. 6 includes a central processing unit (CPU) 602, where computer instructions are processed; a display interface 604 that acts as a communication interface and provides functions for rendering video, graphics, images, and texts on the display; a keyboard interface 606 that provides a communication interface to a keyboard; and a pointing device interface 608 that provides a communication interface to a pointing device, e.g., a touchscreen or presence-sensitive screen. Example implementations of the architecture 600 may include an antenna interface 610 that provides a communication interface to an antenna. Example implementations may include a connection interface 612. The connection interface may include one or more of a peripheral connection interface and network communication interface, providing a communication interface to an external device or network. In certain implementations, a camera interface 614 may be provided that acts as a communication interface and provides functions for capturing digital images from a camera. In certain implementations, a sound interface 616 may be provided as a communication interface for converting sound into electrical signals using a microphone and for converting electrical signals into sound using a speaker. According to example implementations, a random access memory (RAM) 618 may be provided, where computer instructions and data may be stored in a volatile memory device for processing by the CPU 602.

According to an example implementation, the architecture 600 may include a read-only memory (ROM) 620 where invariant low-level system code or data for basic system functions such as basic input and output (I/O), startup, or reception of keystrokes from a keyboard are stored in a non-volatile memory device. According to an example implementation, the architecture 600 may include a storage medium 622 or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system 624, application programs 626 (including, for example, a web browser application, a widget or gadget engine, and or other applications, as necessary) and data files 628 are stored. According to an example implementation, the architecture 600 may include a power source 630 that provides an appropriate alternating current (AC) or direct current (DC) to power components. According to an example implementation, the architecture 600 may include a telephony subsystem 632 that allows the device 600 to transmit and receive sound over a telephone network. The constituent devices and the CPU 602 may communicate with each other over a bus 634.

In accordance with an example implementation, the CPU 602 may have appropriate structure to be a computer processor. In one arrangement, the computer CPU 602 may include more than one processing unit. The RAM 618 may interface with the computer bus 634 to provide quick RAM storage to the CPU 602 during the execution of computing programs such as the operating system application programs, and device drivers. More specifically, the CPU 602 may load computer-executable process steps from the storage medium 622 or other media into a field of the RAM 618 in order to execute computing programs. Data may be stored in the RAM 618, where the data may be accessed by the computer CPU 602 during execution. In one example configuration, the device 600 may include at least 128 MB of RAM, and 256 MB of flash memory.

The storage medium 622 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media may allow the device 600 to access computer-executable process steps, application programs and the like, stored on removable and non-removable memory media, to off-load data from the device 600 or to upload data onto the device 600. A computer program product, such as one utilizing a communication system may be tangibly embodied in storage medium 622, which may comprise a machine-readable storage medium.

In an example implementation of the disclosed technology, the computing system architecture 600 may include any number of hardware and/or software applications 221, 222 that are executed to facilitate any of the operations. In an example implementation, one or more I/O interfaces may facilitate communication between the computing system architecture 600 and one or more input/output devices. For example, a universal serial bus port, a serial port, a disk drive, a CD-ROM drive, and/or one or more user interface devices, such as a display, keyboard, keypad, mouse, control panel, touchscreen display, microphone, etc., may facilitate user interaction with the computing system architecture 600. The one or more I/O interfaces may be utilized to receive or collect data and/or user instructions from a wide variety of input devices. Received data may be processed by one or more computer processors as desired in various implementations of the disclosed technology and/or stored in one or more memory devices.

One or more network interfaces may facilitate connection of the computing system architecture 600 inputs and outputs to one or more suitable networks and/or connections; for example, the connections that facilitate communication with any number of sensors associated with the system. The one or more network interfaces may further facilitate connection to one or more suitable networks; for example, a local area network, a wide area network, the Internet, a cellular network, a radio frequency network, a Bluetooth enabled network, a Wi-Fi enabled network, a satellite-based network any wired network, any wireless network, a proximity network, etc., for communication with external devices and/or systems. As desired, implementations of the disclosed technology may include the computing system architecture 600 with more or less of the components illustrated in FIG. 6.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, may be implemented by computer-executable program instructions. Likewise, some blocks of the block diagrams and flow diagrams may not necessarily need to be performed in the order presented, or may not necessarily need to be performed at all, according to some implementations of the disclosed technology.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that may direct a computer or other programmable data processing apparatus to function in a particular manner, such that the instructions stored in the computer-readable memory produce an article of manufacture including instruction means that implement one or more functions specified in the flow diagram block or blocks. As an example, implementations of the disclosed technology may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
   a processor;
   memory operatively coupled to the processor and configured for storing data and instructions that, when executed by the processor, cause the system to:
   receive a microwave spectrum associated with rotational modes of a communication molecule involved with quorum sensing, the communication molecule located in an environment having a plurality of cells, the microwave spectrum having one or more peaks, each of the one or more peaks corresponding to a frequency on the microwave spectrum; and
   transmit one or more microwave signals to the communication molecule;
   wherein the one or more microwave signals includes a first microwave signal, the frequency of the first microwave signal hopping between frequency ranges corresponding to a first peak and a second peak in the microwave spectrum.

2. A method comprising:
   obtaining a microwave spectrum associated with rotational modes of a communication molecule involved with quorum sensing, the communication molecule located in an environment having a plurality of cells, the microwave spectrum having one or more peaks, each of the one or more peaks corresponding to a frequency on the microwave spectrum; and transmitting one or more microwave signals to the communication molecule, wherein the one or more microwave signals comprises a first microwave signal having a frequency hopping between frequency ranges corresponding to a first peak in the microwave spectrum and a second peak in the microwave spectrum.

3. The method of claim 2, wherein transmitting the one or more microwave signals disrupts the quorum sensing.

4. The method of claim 3, wherein the communication molecule is a 3-oxo-C12 AHL molecule.

5. The method of claim 2, wherein obtaining the microwave spectrum comprises modeling the communication molecule and analytically deriving the spectrum.

6. The method of claim 2, further comprising relating the one or more peaks in the microwave spectrum to a mode of vibration of one or more moieties of the communication molecule; and wherein one or more portions of the communication molecule comprises at least part of the one or more moieties.

7. The method of claim 2, the one or more microwave signals being a substantially continuous signal.

8. The method of claim 2, the one or more microwave signals being a pulsed signal.

9. The method of claim 2, the one or more microwave signals having a frequency bandwidth of less than 101 MHz.

10. The method of claim 2, wherein the power of each of the one or more microwave signals is less than one microwatt.

11. The method of claim 2, wherein the total power of the one or more microwave signals is less than one microwatt.

12. The method of claim 2, wherein transmitting the one or more microwave signals induces a rotation of the communication molecule.

13. The system of claim 1, wherein the memory is operatively coupled to the processor and configured for storing data and instructions that, when executed by the processor, cause the system to transmit the one or more microwave signals to the communication molecule until the quorum sensing is disrupted.

14. The system of claim 13, wherein the communication molecule is a 3-oxo-C12 AHL molecule.

15. The system of claim 1, wherein the one or more microwave signals are a substantially continuous signal.

16. The system of claim 1, wherein one or more microwave signals are a pulsed signal.

17. The system of claim 1, wherein the one or more microwave signals have a frequency bandwidth of less than 101 MHz.

18. The system of claim 1, wherein the power of each of the one or more microwave signals is less than one microwatt.

19. The system of claim 1, wherein the total power of the one or more microwave signals is less than one microwatt.

20. A method comprising:

obtaining a microwave spectrum associated with rotational modes of a communication molecule involved with quorum sensing, the communication molecule located in an environment having a plurality of cells, the microwave spectrum having one or more peaks, each of the one or more peaks corresponding to a frequency on the microwave spectrum; and transmitting one or more microwave signals to the communication molecule, the one or more microwave signals inducing a rotation of the communication molecule and disrupting the quorum sensing, wherein the one or more microwave signals comprises a first microwave signal having a frequency hopping between frequency ranges corresponding to a first peak in the microwave spectrum and a second peak in the microwave spectrum.

\* \* \* \* \*